US009390313B2

(12) United States Patent
Sano et al.

(10) Patent No.: US 9,390,313 B2
(45) Date of Patent: Jul. 12, 2016

(54) IMAGE MEASUREMENT APPARATUS AND IMAGE MEASURMENT METHOD MEASURING THE CELL NECLEI COUNT

(71) Applicant: NEC Corporation, Tokyo (JP)

(72) Inventors: Maki Sano, Tokyo (JP); Yoshiko Yoshihara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 14/395,583

(22) PCT Filed: Mar. 7, 2013

(86) PCT No.: PCT/JP2013/001449
§ 371 (c)(1),
(2) Date: Oct. 20, 2014

(87) PCT Pub. No.: WO2013/161155
PCT Pub. Date: Oct. 31, 2013

(65) Prior Publication Data
US 2015/0131854 A1 May 14, 2015

(30) Foreign Application Priority Data
Apr. 23, 2012 (JP) ................................. 2012-097561

(51) Int. Cl.
*G06K 9/00* (2006.01)
*G06T 7/00* (2006.01)
(Continued)

(52) U.S. Cl.
CPC .......... *G06K 9/0014* (2013.01); *G01N 15/1475* (2013.01); *G06T 7/0012* (2013.01); *G06T 7/0081* (2013.01); *G06T 7/0091* (2013.01);
(Continued)

(58) Field of Classification Search
None
See application file for complete search history.

(56) References Cited

U.S. PATENT DOCUMENTS 7,219,016 B2  5/2007  Rimm et al.
7,873,480 B2  1/2011  Rimm et al.
(Continued)

FOREIGN PATENT DOCUMENTS

JP  9-138854  5/1997
JP  2004-532410  10/2004
(Continued)

OTHER PUBLICATIONS

Japanese Office Action dated Sep. 15, 2015 in corresponding Japanese Patent Application No. 2014-512308 with partial English translation of Japanese Office Action.

*Primary Examiner* — Jason Heidemann
(74) *Attorney, Agent, or Firm* — Young & Thompson

(57) ABSTRACT

A partial image extracting unit extracts images of a predetermined size and constant magnification from a tissue region. A mask generating unit generates a mask for removing a region not intended for measurement from the tissue region for each extracted image. A complete mask generating unit generates a temporary complete mask in which the masks generated for each of the images are integrated together, and generates a complete mask in which close portions among unmasked portions in the temporary complete mask are unified into one or more target regions. A measuring unit measures information pertaining to an object to be measured included in the image, and this information is measured for each of the images extracted by the partial image extracting unit. A region information calculating unit calculates, for each target region, information pertaining to the object to be measured from the measured information and from the complete mask.

8 Claims, 5 Drawing Sheets

(51) Int. Cl.
 *G01N 15/14* (2006.01)
 *G01N 15/10* (2006.01)

(52) U.S. Cl.
 CPC ............. *G01N 2015/1006* (2013.01); *G06T 2207/20021* (2013.01); *G06T 2207/20036* (2013.01); *G06T 2207/30096* (2013.01); *G06T 2207/30224* (2013.01); *G06T 2207/30242* (2013.01)

(56) References Cited

U.S. PATENT DOCUMENTS

| | | | |
|---|---|---|---|
| 7,989,209 B2 * | 8/2011 | Marcelpoil | G01N 1/30 382/100 |
| 8,036,833 B2 | 10/2011 | Rimm et al. | |
| 8,121,794 B2 | 2/2012 | Rimm et al. | |
| 8,185,320 B2 | 5/2012 | Rimm et al. | |
| 8,265,370 B2 | 9/2012 | Ducksbury et al. | |
| 8,486,704 B2 * | 7/2013 | Marcelpoil | G01N 1/30 338/20 |
| 8,492,156 B2 * | 7/2013 | Marcelpoil | G01N 1/30 382/128 |
| 8,594,411 B2 | 11/2013 | Yoshihara et al. | |
| 8,639,450 B2 | 1/2014 | Rimm et al. | |
| 9,031,294 B2 | 5/2015 | Nosato et al. | |
| 9,076,198 B2 | 7/2015 | Yoshihara et al. | |
| 2002/0081014 A1 * | 6/2002 | Ravkin | G01N 15/1475 382/134 |
| 2007/0026525 A1 * | 2/2007 | Marcelpoil | G01N 1/30 436/63 |
| 2010/0061618 A1 * | 3/2010 | Marcelpoil | G01N 1/30 382/133 |
| 2010/0067774 A1 * | 3/2010 | Marcelpoil | G01N 1/30 382/133 |
| 2010/0067775 A1 * | 3/2010 | Marcelpoil | G01N 1/30 382/133 |
| 2010/0303809 A1 * | 12/2010 | Bacus | A61K 31/517 424/133.1 |
| 2013/0011036 A1 | 1/2013 | Marugame et al. | |
| 2013/0182936 A1 * | 7/2013 | Yoshihara | G06T 7/0081 382/133 |
| 2013/0230230 A1 * | 9/2013 | Ajemba | G06T 7/0012 382/133 |
| 2013/0338016 A1 * | 12/2013 | McDonough | G06F 19/18 506/8 |
| 2015/0030219 A1 * | 1/2015 | Madabhushi | G06T 7/0083 382/128 |

FOREIGN PATENT DOCUMENTS

| | | |
|---|---|---|
| JP | 2005-530138 | 10/2005 |
| JP | 2009-508200 | 2/2009 |
| JP | 2010-281636 | 12/2010 |
| JP | 2011-210156 | 10/2011 |
| WO | 2012/011579 | 1/2012 |
| WO | 2012/043498 | 4/2012 |

* cited by examiner

| ROI | Negative | Positive | Total | % |
|---|---|---|---|---|
| A | 2100 | 27900 | 30000 | 93.0 |
| B | 35970 | 5280 | 41250 | 12.8 |
| ALL | 38070 | 33180 | 71250 | 46.6 |

IMAGE MEASUREMENT APPARATUS AND IMAGE MEASURMENT METHOD MEASURING THE CELL NECLEI COUNT

TECHNICAL FIELD

The present invention relates to an image measurement apparatus, image measurement method, and image measuring program which measure information on an object contained in tissue from a stained tissue sample image.

BACKGROUND ART

Measuring the number of cell nuclei contained in a region of an object (e.g. cancer) from an immuno-histochemistry (IHC) sample image has been carried out. In general, when a user such as a technician and a pathologist specifies a measurement object region in an IHC sample image, a system for image measurement measures, for example, a cell nuclei count in the specified region according to staining intensity.

In NPL 1, a method to automatically recognize cell nuclei equivalent to a learned cell nucleus from an entire sample tissue region is disclosed. In NPL 2, a method to determine staining intensities and compute a cell nuclei count according to staining intensity for cell nuclei automatically recognized by the method described in NPL 1 is disclosed.

FIG. 5 is an explanatory diagram illustrating a recognition result of a measurement object by the method described in NPL 1. FIG. 5 illustrates that results of recognition of specified measurement object tissue are individually displayed.

In PTL 1, a breast cancer pathologic image diagnosis supporting system which computes a stained positive cell content rate is disclosed. The system described in PTL 1 matches a tumor region acquired from HE (Hematoxylin and Eosin stain) stained image to a tumor region in the IHC image, and, based on information of the tumor region in the IHC image identified through the matching, computes stained positive cell content rate in the tumor region.

CITATION LIST

Patent Literature

PTL 1: International Publication No. WO2008/108059

Non Patent Literature

NPL 1: Aperio, "GENIE TISSUE PATTERN RECOGNITION",
NPL 2: Kate Lillard-Wetherell, Ph.D., "Automated selection and analysis of tumor regions in breast sections stained with nuclear IHC biomarkers", APERIO, APERIO APPLICATION NOTE, October 2008.

SUMMARY OF INVENTION

Technical Problem

In a general method, when, for example, the number of cell nuclei in an object region is measured, a user is required to recognize a measurement object from an IHC sample image and specify a measurement object region. Accordingly, there is a problem such that the user takes extra effort.

When an entire tissue region is specified as a measurement object by using a method described in NPL 2, measurement values acquired as computation results such as a staining intensity or a positive or negative result of every cell nucleus are used as one value aggregated over the entire tissue region. In this case, it is hard, for example, to observe a staining heterogeneity in each cancerous region as an individual value.

For example, it is possible for a user to understand a distribution of individual measurement object cell nuclei from an IHC sample image by referring to a recognition result by the method described in NPL 1. However, it is difficult for the user to understand a meaning the recognized measurement object region has, such as stainability of the region, from information illustrated in FIG. 5 alone.

Accordingly, an object of the present invention is to provide an image measurement apparatus, image measurement method, and image measuring program that makes it possible to measure information indicated by an object region from an image showing a tissue sample in an easily understandable manner for a user.

Solution to Problem

One aspect of the present invention is an image measurement apparatus which includes:

tissue region recognition means configured to recognize a tissue region from an image which is imaged by staining tissue including a measurement object and a non-measurement object;

partial image extraction means configured to extract images of an predetermined size and a fixed magnification from the tissue region;

mask generation means configured to generate a mask to remove a non-measurement object region, which is a region in which the non-measurement object exists, from the tissue region for each of the extracted images;

whole mask generation means configured to generate a provisional whole mask by merging masks generated for each of the images and generate a whole mask by merging portions which are not masked in the provisional whole mask, the portions adjacent to each other into one or more object regions;

measurement means configured to measure, for each of the images extracted by the partial image extraction means, information on the measurement object contained in the images; and region information computation means configured to compute, based on the measured information and the whole mask, information on the measurement object for each of the object regions.

One aspect of the present invention is an image measurement method which includes:

recognizing a tissue region from an image which is imaged by staining tissue including a measurement object and a non-measurement object;

extracting images of a predetermined size and a fixed magnification from the tissue region;

generating a mask to remove a non-measurement object region, which is a region in which the non-measurement object exists, from the tissue region for each of the extracted images;

generating a provisional whole mask by merging masks each of which is generated for each of the images;

generating a whole mask by merging portions which are not masked in the provisional whole mask, the portions adjacent to each other into one or more object regions;

measuring, for each of the images extracted from the tissue region, information on the measurement object contained in the image; and computing, based on the measured information and the whole mask, information on the measurement object for each of the object regions.

One aspect of the present invention is an non-transitory computer-readable storage medium storing an image measuring program which causes a computer to execute:

a tissue region recognition process of recognizing a tissue region from an image which is imaged by staining tissue including a measurement object and a non-measurement object;

a partial image extraction process of extracting images of a predetermined size and a fixed magnification from the tissue region;

a mask generation process of generating a mask to remove a non-measurement object region, which is a region in which the non-measurement object exists, from the tissue region for each of the extracted images;

a whole mask generation process of generating a provisional whole mask by merging masks generated for each of the images and generating a whole mask by merging portions which are not masked in the provisional whole mask, the portions adjacent to each other into one or more object regions;

a measurement process of measuring, for each of the images extracted in the partial image extraction process, information on the measurement object contained in the image; and a region information computation process of computing, based on the measured information and the whole mask, information on the measurement object for each of the object regions.

Advantageous Effects of Invention

With the present invention, it becomes possible to measure information indicated by an object region from an image showing a tissue sample in an easily understandable manner for a user.

DESCRIPTION OF EMBODIMENTS

An exemplary embodiment of the present invention will be described below with reference to the accompanying drawings.

Figure 1:
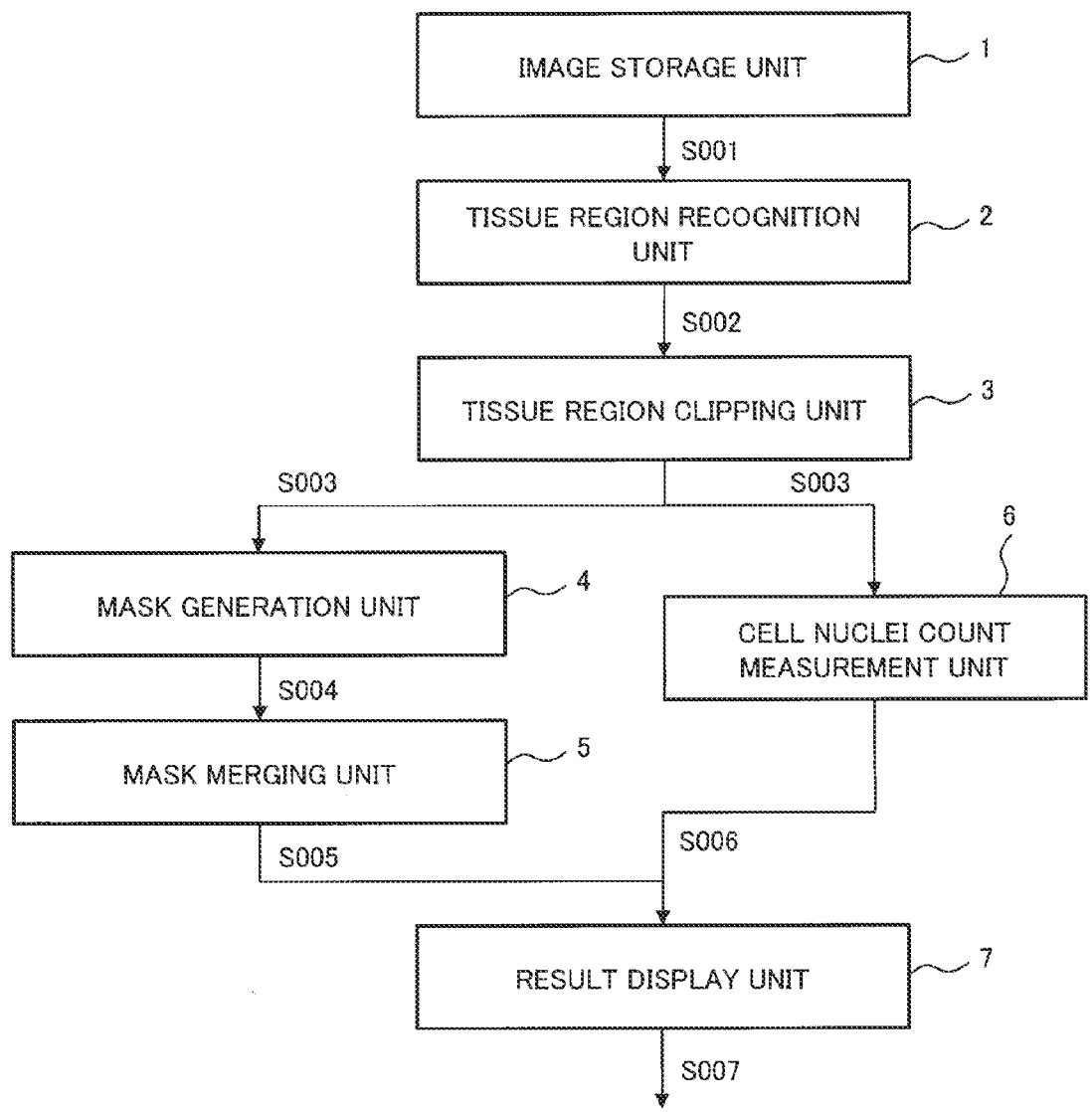
FIG. 1 is a block diagram illustrating an exemplary embodiment of an image measurement apparatus according to the present invention.

FIG. 1 is a block diagram illustrating an exemplary embodiment of an image measurement apparatus according to the present invention. The image measurement apparatus of the exemplary embodiment includes an image storage unit 1, a tissue region recognition unit 2, a tissue region clipping unit 3, a mask generation unit 4, a mask merging unit 5, a cell nuclei count measurement unit 6, and a result display unit 7.

The image storage unit 1 stores a scanned image S001 of a tissue sample. The scanned image of the tissue sample includes, for example, an image of an immuno-histochemistry sample or the like. A tissue sample image contains various components. Examples of the component include a cancerous region (cancerous region with no distinction of existence of an invasion), cancerous region with invasion, cancerous region without invasion, benign disease region, normal region without lesion, gland duct region, blood vessel region, lymphatic region, epithelial region, interstitial region, lymphocyte, artifact region, necrotic region, fatty region, and so on. However, the component is not limited to these items.

These components are categorized into components which are objects of measurement (hereinafter, each referred to as a measurement object) and components which are not objects of measurement (hereinafter, each referred to as a non-measurement object) in advance in accordance with the purpose of the system. For example, a "cancerous region without invasion" may be either a measurement object or a non-measurement object depending on the purpose of the system. The image storage unit 1 is configured with, for example, a magnetic disk or the like.

In the exemplary embodiment, a case in which the image measurement apparatus includes the image storage unit 1 will be described as an example. The image measurement apparatus may be configured so as to receive an image of an imaged tissue sample from another apparatus. In this case, the image measurement apparatus may not include the image storage unit 1.

The tissue region recognition unit 2 recognizes a whole tissue region S002 (may also be referred to as a tissue region) from the image S001 stored on the image storage unit 1. In general, a tissue sample image includes a region which is not a tissue sample image (e.g. slide glass or the like) other than the above-described measurement objects and non-measurement objects. Thus, the tissue region recognition unit 2 may recognize the tissue region by removing portions which do not correspond to the tissue sample image from the image S001.

The tissue region clipping unit 3 clips images S003 of a fixed magnification and a fixed size from the image of the whole tissue region S002 which is recognized by the tissue region recognition unit 2. Specifically, the tissue region clipping unit 3 extracts the images S003 of a fixed magnification and a predetermined size from the tissue region.

The mask generation unit 4 recognizes regions where a non-measurement object exists (hereinafter, referred to as non-measurement object regions) for each image clipped by the tissue region clipping unit 3 (i.e. image S003), and computes masks S004. Specifically, the mask generation unit 4 generates a mask S004 to remove the non-measurement object regions from the tissue region for each clipped image. For example, in case interstitial cells are the non-measurement objects, the mask generation unit 4 may recognize regions containing the interstitial cells and compute the mask for each image S003.

A method to generate the mask for each clipped image will be described below by taking a case in which interstitial cells are non-measurement objects as an example. In general, a tissue sample image is often a color image. Hence, the mask generation unit 4 converts the tissue sample image to a grayscale image. The mask generation unit 4 carries out smoothing processing such as Gaussian filtering to the converted grayscale image. With this processing, density differences decrease in the regions containing measurement objects, causing the regions to be combined into a lump. On the other hand, in the interstitial regions, the brightness values of discretely-distributed stained interstitial cell nuclei increase to higher brightness values influenced by surrounding pixels that have high brightness values.

The mask generation unit 4 generates a brightness value histogram of the image to which the smoothing processing is carried out, and computes a threshold value for separating the interstitial region and the measurement object region. The mask generation unit 4 may compute the threshold value by, for example, dynamic programming. The mask generation unit 4 generates the mask by carrying out binarization processing based on the threshold value.

Methods to generate the mask are not limited to the above-described method. As long as it is a method by which a region where a non-measurement object exists in the tissue sample image (tissue region) can be identified, the mask generation unit 4 may generate masks by using other methods.

The mask merging unit 5 generates a whole mask S005 corresponding to the whole tissue region by merging all masks, each of which is computed for each clipped image.

Specifically, the mask merging unit 5 merges the masks each of which is generated for each clipped image. Hereinafter, the merged mask is referred to as a provisional whole mask. The mask merging unit 5 generates the whole mask by merging portions adjacent to each other among portions not masked in the provisional whole mask into one or more object regions.

The unmasked portions correspond to measurement object portions in the tissue sample image. Accordingly, merging the adjacent unmasked portions is equivalent to merging adjacent measurement object portions in the tissue sample image. In this way, measurement objects in the tissue sample image are merged into several object regions. In other words, it can be said that the mask merging unit 5 organizes a tissue sample image into meaningful regions by generating such object regions.

The mask merging unit 5 carries out image processing to the provisional whole mask so as to generate the above-described object regions. The mask merging unit 5 may, for example, generate each object region by carrying out image processing such as expansion processing, reduction processing, closing processing, opening processing, fill-up processing, and small region deletion processing to the provisional whole mask. With this method, it is possible to organize measurement object regions in the tissue sample image into meaningful regions such as, for example, a cancerous region.

The cell nuclei count measurement unit 6 measures a cell nuclei count according to staining intensity for each image clipped by the tissue region clipping unit 3 (i.e. image S003). Hereinafter, information indicating the cell nuclei count according to staining intensity measured by the cell nuclei count measurement unit 6 is referred to as cell nuclei count measurement information S006. The cell nuclei count according to staining intensity is an example of information measured by the cell nuclei count measurement unit 6. The cell nuclei count measurement unit 6 may measure other information on the measurement object contained in images clipped by the tissue region clipping unit 3.

The result display unit 7 outputs a result for each measurement object region such as a cancerous region. Specifically, the result display unit 7 computes information on the measurement object for each object region based on the information measured by the cell nuclei count measurement unit 6 and the whole mask.

The result display unit 7, for example, computes a measurement result of the cell nuclei count according to staining intensity and a positive ratio for each cancerous region based on the whole mask S005 corresponding to the whole tissue region and cell nuclei count measurement information S006. The result display unit 7 then displays a result image S007 indicating the computation result. The result display unit 7 may output information on the measurement object for each object region by, for example, superimposing the object region on the scanned image S001 of the tissue sample.

Figure 2:
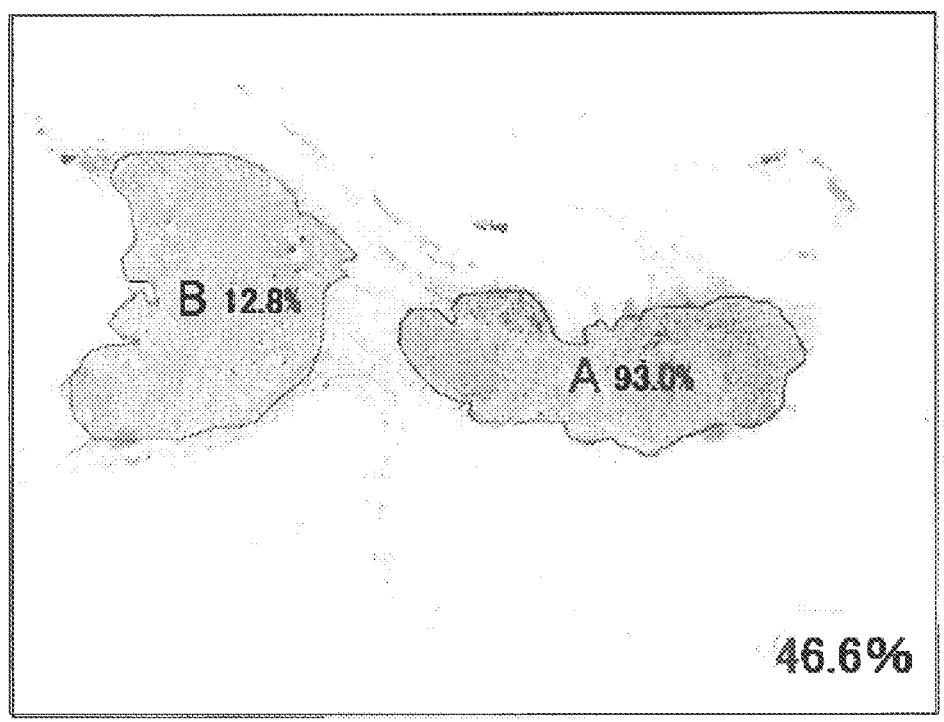
FIG. 2 is a diagram illustrating an example of an output result by a result display unit.

FIG. 2 is an explanatory diagram illustrating an example of the result image S007 output by the result display unit 7. FIG. 2 illustrates an example in which there are two object regions of a measurement object (e.g. cancer) and positive ratios associated with each object region and the whole region are displayed.

As described above, in the exemplary embodiment, measurement objects are organized into meaningful regions. Accordingly, displaying a cell nuclei count according to staining intensity and a positive ratio for each region makes it possible to observe a stain heterogeneity for each cancerous region in the whole tissue region. In the exemplary embodiment, it is also possible to acquire an area distribution (histogram) of a positive ratio only for measurement object regions in the whole tissue region because the size of the measurement object regions is determined.

The tissue region recognition unit 2, the tissue region clipping unit 3, the mask generation unit 4, the mask merging unit 5, the cell nuclei count measurement unit 6, and the result display unit 7 are implemented by a CPU of a computer which operates according to a program (image measurement program). For example, the program may be stored in a storage unit (not illustrated) in the image measurement apparatus, and the CPU may read in the program, and, by following the program, operate as the tissue region recognition unit 2, the tissue region clipping unit 3, the mask generation unit 4, the mask merging unit 5, the cell nuclei count measurement unit 6, and the result display unit 7. Moreover, each of the tissue region recognition unit 2, the tissue region clipping unit 3, the mask generation unit 4, the mask merging unit 5, the cell nuclei count measurement unit 6, and the result display unit 7 may be implemented by dedicated hardware.

Figure 3:
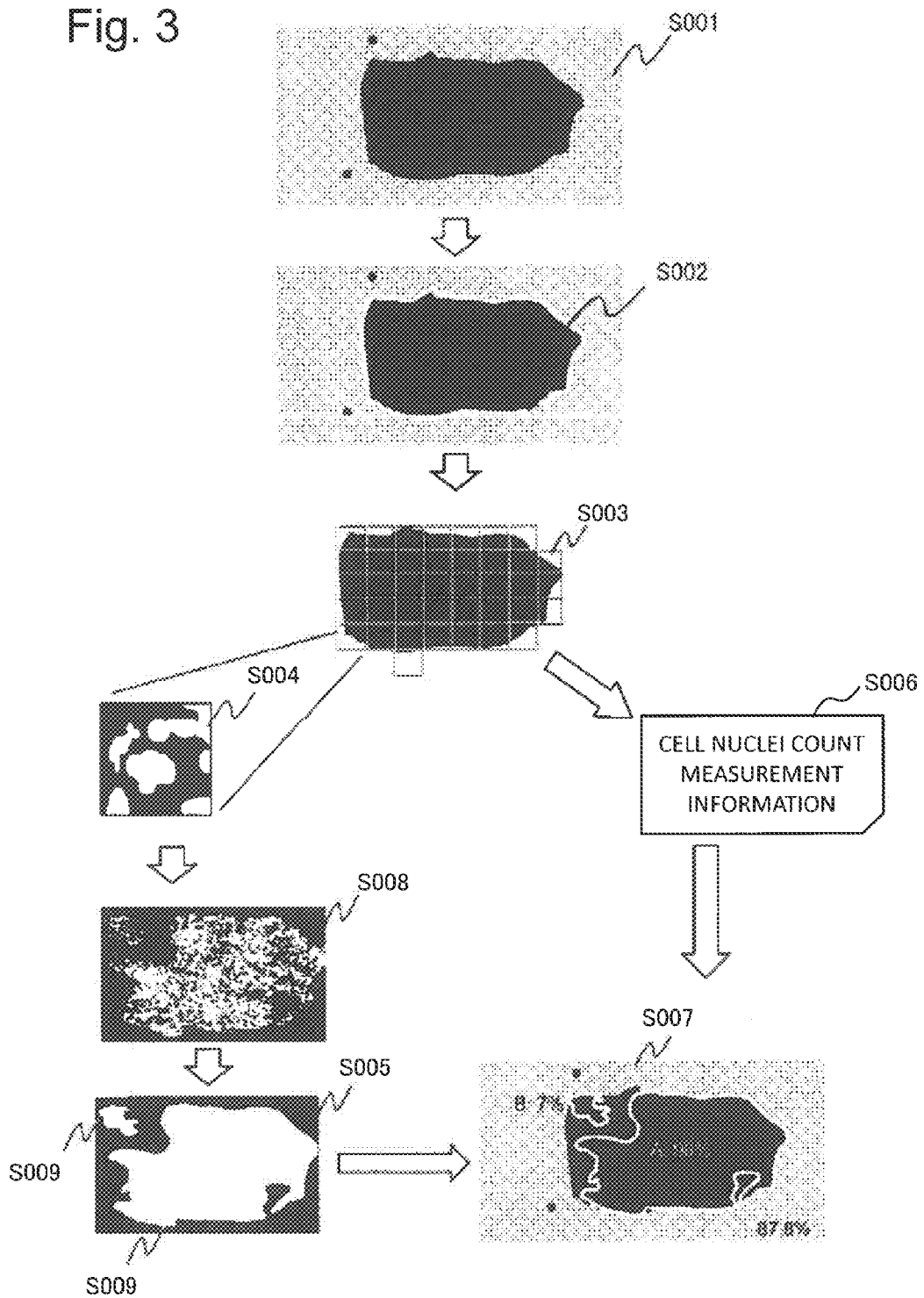
FIG. 3 is an explanatory diagram illustrating an example of an operation of displaying a positive ratio for each region showing a measurement object.

Next, an operation of the image measurement apparatus of the exemplary embodiment will be described below. FIG. 3 is an explanatory diagram illustrating an example of an operation to display a positive ratio for each region indicating a measurement object from a scanned image of a tissue sample.

When a scanned image S001 is input, the tissue region recognition unit 2 recognizes a tissue region S002 from the image S001.

The tissue region clipping unit 3 extracts images S003 of a fixed magnification and a predetermined size from the tissue region S002.

The mask generation unit 4 generates a mask S004 for each extracted image S003.

The mask merging unit 5 generates a provisional whole mask S008 by merging the masks S004 each of which is generated for each image S003. The mask merging unit 5 generates a whole mask S005 by merging unmasked portions adjacent to each other in the provisional whole mask S008 into one or more object regions S009. In other words, each object region S009 is a region generated by carrying out image processing such as expansion processing to portions indicated in white in the provisional whole mask S008, and is included in the whole mask S005.

On the other hand, the cell nuclei count measurement unit 6 measures information on the measurement object contained in each image S003. The cell nuclei count measurement unit 6, for example, generates cell nuclei count measurement information S006 by, for example, measuring the number of cell nuclei contained in each image S003 according to staining intensity.

The result display unit 7 computes information on the measurement object (e.g. cancer) for each object region S009 based on the measured information (cell nuclei count measurement information S006) and the whole mask S005. The result display unit 7, for example, computes a measurement result of the cell nuclei count according to staining intensity and a positive ratio for each object region S009. The result display unit 7 then outputs the computation result.

As described above, according to the exemplary embodiment, the tissue region recognition unit 2 recognizes a tissue region S002 from a scanned image S001 of a tissue sample (e.g. IHC sample image). The tissue region clipping unit 3 extracts images S003 of a fixed magnification and a predetermined size from the tissue region S002. The mask generation unit 4 generates a mask S004 to remove a non-measurement object region from the tissue region for each extracted image S003. The mask merging unit 5 generates a provisional whole mask S008 into which the masks S004 are merged.

The mask merging unit 5 also generates a whole mask S005 by merging unmasked portions adjacent to each other in the provisional whole mask S008 into one or more object regions S009.

On the other hand, the cell nuclei count measurement unit 6, for each image S003 extracted from the tissue region, measures information S006 (e.g. cell nuclei count according to staining intensity) on a measurement object (e.g. cancer) contained in the image. The result display unit 7 computes information on the measurement object (e.g. a measurement result of a cell nuclei count according to staining intensity and a positive ratio) for each object region S009 based on the measured information S006 and the whole mask S005.

With the above-described configuration, it is possible to measure items of information indicated by an object region in an easily understandable manner for a user from an image showing a tissue sample.

Specifically, by using the image measurement apparatus of the exemplary embodiment, it is possible to save the user time and effort because a region to be measured needs not be selected in advance. Because a difference between users in selection of measurement object regions is mitigated, deviation in a determination is also eliminated, which makes it possible to carry out a quantitative measurement of an object. Moreover, because stain heterogeneity for each cancerous region can be displayed on an IHC sample and an area distribution (histogram) of a positive ratio can be computed only for a cancerous region in the whole tissue region, it is possible to support a pathologist to determine a medical treatment.

Figure 5:
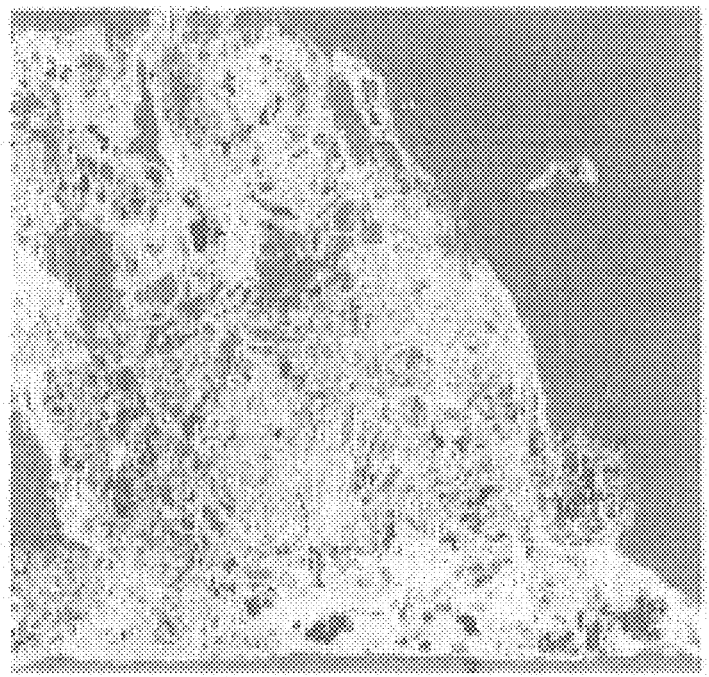
FIG. 5 is an explanatory diagram illustrating a recognition result of a measurement object by a method disclosed in NPL 1.

For example, in a case of a result illustrated in FIG. 5, because each region element is too small to display a cell nuclei count and a positive ratio, it is difficult for a user to understand the result. As a consequence, although the region (distribution) of a measurement object is viewable, only one value corresponding to a whole of a sample or a whole of a specified region is virtually viewable for each of a cell nuclei count and a positive ratio.

However, in the exemplary embodiment, it is possible to display the image exemplified in FIG. 2. In this way, in the exemplary embodiment, it is possible to display items of information indicated by an object region from an image showing a tissue sample in an easily understandable manner for a user.

Figure 4:
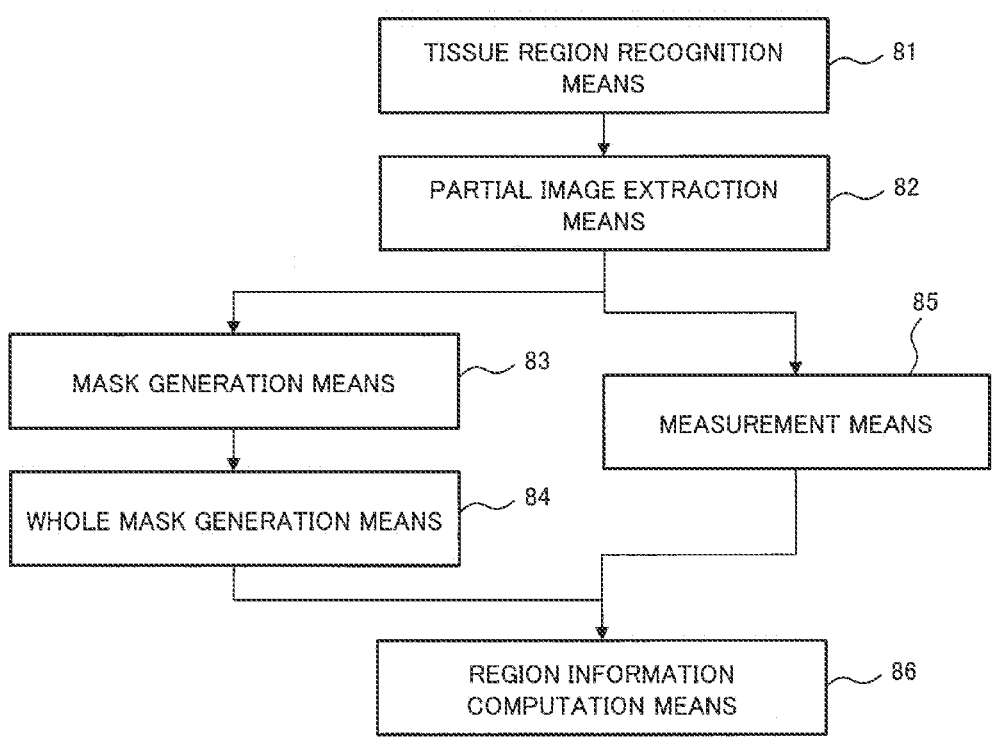
FIG. 4 is a block diagram illustrating a configuration of the image measurement apparatus according to the present invention.

Next, a configuration of the present invention will be described below. FIG. 4 is a block diagram illustrating a configuration of the image measurement apparatus according to the present invention. The image measurement apparatus according to the present invention includes a tissue region recognition means 81 (e.g. tissue region recognition unit 2) configured to recognize a tissue region from an image (e.g. IHC sample image) which is imaged by staining tissue containing a measurement object (e.g. cancer) and a non-measurement object, a partial image extraction means 82 (e.g. tissue region clipping unit 3) configured to extract images of a fixed magnification and a predetermined size from the tissue region, a mask generation means 83 (e.g. mask generation unit 4) configured to generate a mask to remove a non-measurement object region, which is a region in which a non-measurement object exists, from the tissue region for each of the extracted images, a whole mask generation means 84 (e.g. mask merging unit 5) configured to generate a provisional whole mask by merging the masks each generated for every image and generate a whole mask by merging portions adjacent to each other among unmasked portions in the provisional whole mask into one or more object regions, a measurement means 85 (e.g. cell nuclei count measurement unit 6) configured to, for each of the images extracted by the partial image extraction means 82, measure information on the measurement object contained in the image (e.g. cell nuclei count according to staining intensity), and a region information computation means 86 (result display unit 7) configured to compute information on the measurement object (e.g. measurement result of a cell nuclei count according to staining intensity and a positive ratio) for each object region based on the measured information and the whole mask.

With such a configuration, it is possible to measure information indicated by an object region from an image showing a tissue sample in an easily understandable manner for a user.

The measurement means 85 may measure the cell nuclei count according to staining intensity for each image extracted by the partial image extraction means 82. The region information computation means 86 may compute a measurement result of the cell nuclei count according to staining intensity for each object region based on the measured cell nuclei count according to staining intensity and the whole mask.

Furthermore, the region information computation means 86 may compute the positive ratio for each object region based on the measured cell nuclei count according to staining intensity and the whole mask.

The image measurement apparatus may include an output means (e.g. result display unit 7) configured to output the information on the measurement object for each object region, which is computed by the region information computation means 86, and an image, which is imaged by staining the tissue, in association with the object region.

Although the present invention has been described with reference to an exemplary embodiment and examples thereof, it should be understood that the present invention is not limited to the above-described exemplary embodiment and examples. To the configuration and detail of the present invention, various modifications apparent to those skilled in the art may be applied without departing from the scope of the invention.

This application claims priority from Japanese Patent Application No. 2012-097561, filed on Apr. 23, 2012, the contents of which are hereby incorporated by reference in their entirety as if fully set forth herein.

INDUSTRIAL APPLICABILITY

The present invention is suitably applied to an image measurement apparatus that measures information on an object contained in tissue from an image of a stained tissue sample.

REFERENCE SIGNS LIST

1 Image storage unit
2 Tissue region recognition unit
3 Tissue region clipping unit
4 Mask generation unit
5 Mask merging unit
6 Cell nuclei count measurement unit
7 Result display unit

The invention claimed is:

1. An image measurement apparatus, comprising:
a tissue region recognition unit configured to recognize a tissue region from an image which is imaged by staining tissue including a measurement object and a non-measurement object;
a partial image extraction unit configured to extract images of a predetermined size and a fixed magnification from the tissue region;
a mask generation unit configured to generate a mask to remove a non-measurement object region, which is a region in which the non-measurement object exists, from the tissue region for each of the extracted images;
a whole mask generation unit configured to generate a provisional whole mask by merging masks generated for each of the images and generate a whole mask by merging portions which are not masked in the provisional whole mask, the portions adjacent to each other into one or more object regions;
a measurement unit configured to measure, for each of the images extracted by the partial image extraction unit, information on the measurement object contained in the images; and
a region information computation unit configured to compute, based on the measured information and the whole mask, information on the measurement object for each of the object regions,
wherein the measurement unit measures the cell nuclei count according to staining intensity for each of the images extracted by the partial image extraction unit, and
the region information computation unit computes, based on the measured cell nuclei count according to staining intensity and the whole mask, a positive ratio for each of the object regions.

2. The image measurement apparatus according to claim 1, further comprising
an output unit configured to output information on the measurement object for each of the object regions, which is computed by the region information computation unit, with the image which is imaged by staining tissue in association with the object region.

3. An image measurement method, comprising:
recognizing a tissue region from an image which is imaged by staining tissue including a measurement object and a non-measurement object;
extracting images of a predetermined size and a fixed magnification from the tissue region;
generating a mask to remove a non-measurement object region, which is a region in which the non-measurement object exists, from the tissue region for each of the extracted images;
generating a provisional whole mask by merging masks each of which is generated for each of the images;
generating a whole mask by merging portions which are not masked in the provisional whole mask, the portions adjacent to each other into one or more object regions;
measuring, for each of the images extracted from the tissue region, information on the measurement object contained in the image; and
computing, based on the measured information and the whole mask, information on the measurement object for each of the object regions,
wherein, for each of the images extracted from the tissue region, the cell nuclei count according to staining intensity is measured, and
based on the measured cell nuclei count according to staining intensity and the whole mask, a positive ratio for each of the object regions is computed.

4. The image measurement method according to claim 3,
based on the measured cell nuclei count according to staining intensity and the whole mask, a measurement result of the cell nuclei count according to staining intensity for each of the object regions is computed.

5. A non-transitory computer-readable storage medium storing an image measuring program which causes a computer to execute:
a tissue region recognition process of recognizing a tissue region from an image which is imaged by staining tissue including a measurement object and a non-measurement object;
a partial image extraction process of extracting images of a predetermined size and a fixed magnification from the tissue region;
a mask generation process of generating a mask to remove a non-measurement object region, which is a region in which the non-measurement object exists, from the tissue region for each of the extracted images;
a whole mask generation process of generating a provisional whole mask by merging masks generated for each of the images and generating a whole mask by merging portions which are not masked in the provisional whole mask, the portions adjacent to each other into one or more object regions;
a measurement process of measuring, for each of the images extracted in the partial image extraction process, information on the measurement object contained in the image; and
a region information computation process of computing, based on the measured information and the whole mask, information on the measurement object for each of the object regions, and
the program causing a computer to:
in the measuring process, for each of the images extracted in the partial image extraction process, measure the cell nuclei count according to staining intensity; and
in the region information computation process, based on the measured cell nuclei count according to staining intensity and the whole mask, compute a positive ratio for each of the object regions.

6. The non-transitory computer-readable storage medium according to claim 5, the program causing a computer to:
in the region information computation process, based on the measured cell nuclei count according to staining intensity and the whole mask, compute a measurement result of the cell nuclei count according to staining intensity for each of the object regions.

7. An image measurement apparatus, comprising:
a tissue region recognition unit configured to recognize a tissue region from an image which is imaged by staining tissue including a measurement object and a non-measurement object;
a partial image extraction unit configured to extract images of a predetermined size and a fixed magnification from the tissue region;
a mask generation unit configured to generate a mask to remove a non-measurement object region, which is a region in which the non-measurement object exists, from the tissue region for each of the extracted images;
a whole mask generation unit configured to generate a provisional whole mask by merging masks generated for each of the images and generate a whole mask by merging portions which are not masked in the provisional whole mask, the portions adjacent to each other into one or more object regions;
a measurement unit configured to measure, for each of the images extracted by the partial image extraction unit, information on the measurement object contained in the images; and
a region information computation unit configured to compute, based on the measured information and the whole mask, information on the measurement object for each of the object regions,
wherein the measurement unit measures a cell nuclei count according to staining intensity for each of the images extracted by the partial image extraction unit, and
the region information computation unit computes, based on the measured cell nuclei count according to staining intensity and the whole mask, a measurement result of the cell nuclei count according to staining intensity for each of the object regions, and
wherein the measurement unit measures the cell nuclei count according to staining intensity for each of the images extracted by the partial image extraction unit, and
the region information computation unit computes, based on the measured cell nuclei count according to staining intensity and the whole mask, a positive ratio for each of the object regions.

8. The image measurement apparatus according to claim 7, further comprising
an output unit configured to output information on the measurement object for each of the object regions, which is computed by the region information computation unit, with the image which is imaged by staining tissue in association with the object region.

* * * * *